US010722652B2

(12) United States Patent
Farmer et al.

(10) Patent No.: US 10,722,652 B2
(45) Date of Patent: Jul. 28, 2020

(54) AUTOMATIC INJECTION DEVICE WITH PLUNGER VELOCITY REGULATOR

(71) Applicant: Owen Mumford Limited, Oxford (GB)

(72) Inventors: Matthew Farmer, Oxford (GB); Oliver Gould, Oxford (GB)

(73) Assignee: Owen Mumford Limited, Oxford (GB)

(*) Notice: Subject to any disclaimer, the term of this patent is extended or adjusted under 35 U.S.C. 154(b) by 275 days.

(21) Appl. No.: 15/576,553

(22) PCT Filed: May 20, 2016

(86) PCT No.: PCT/GB2016/051471
§ 371 (c)(1),
(2) Date: Nov. 22, 2017

(87) PCT Pub. No.: WO2016/189286
PCT Pub. Date: Dec. 1, 2016

(65) Prior Publication Data
US 2018/0147352 A1 May 31, 2018

(30) Foreign Application Priority Data

May 22, 2015 (GB) .................................. 1508862.8

(51) Int. Cl.
*A61M 5/20* (2006.01)
*A61M 5/32* (2006.01)

(52) U.S. Cl.
CPC ........ *A61M 5/2033* (2013.01); *A61M 5/3204* (2013.01); *A61M 2005/206* (2013.01);
(Continued)

(58) Field of Classification Search
CPC .............. A61M 5/2033; A61M 5/3204; A61M 2005/2013; A61M 2005/206; A61M 2005/2086; A61M 2005/14533
See application file for complete search history.

(56) References Cited

U.S. PATENT DOCUMENTS

| 2005/0222539 A1 | 10/2005 | Gonzales et al. | |
| 2010/0036320 A1* | 2/2010 | Cox | A61M 5/24 604/135 |
| 2011/0054412 A1* | 3/2011 | Eich | A61M 5/20 604/207 |

FOREIGN PATENT DOCUMENTS

| EP | 2399627 A1 | 12/2011 |
| GB | 2487235 A | 7/2012 |

(Continued)

OTHER PUBLICATIONS

International Search Report & Written Opinion for International Application No. PCT/GB2016/051471, dated Sep. 7, 2016, 14 pages.
(Continued)

*Primary Examiner* — Nathan R Price
*Assistant Examiner* — Dung T Ulsh
(74) *Attorney, Agent, or Firm* — Quarles & Brady LLP

(57) ABSTRACT

The invention provides an injection device for delivering a dose of medicament from a syringe. The injection device comprises a housing (10), a plunger (110) moveably mounted within the housing, an actuation mechanism (120, 122) arranged to provide a forward biasing force to urge the plunger forward in use to express a dose of medicament and a trigger mechanism (40) arranged to (directly or indirectly) releaseably hold the plunger against the force of the actuation mechanism. The injection device further comprises a plunger velocity regulator comprising a cam surface (162) associated with one of the housing or the plunger, and a cam member (152) associated with the other of the plunger or the housing and arranged to engage the cam surface during actuation movement of the plunger such that axial movement of the plunger relative to the housing causes relative (Continued)

rotational movement of the cam member and limits the forward velocity of the plunger movement.

17 Claims, 6 Drawing Sheets

(52) U.S. Cl.
CPC ............... *A61M 2005/2013* (2013.01); *A61M 2005/2086* (2013.01)

(56) References Cited

FOREIGN PATENT DOCUMENTS

| | | |
|---|---|---|
| WO | WO2010066590 A1 | 6/2010 |
| WO | WO2011162686 A1 | 12/2011 |
| WO | WO2012085580 A1 | 6/2012 |
| WO | WO2014166918 A1 | 10/2014 |
| WO | WO2015011488 A1 | 1/2015 |

OTHER PUBLICATIONS

Search Report for United Kingdom Application No. GB1508862.8, dated Dec. 3, 2015, 3 pages.

* cited by examiner

AUTOMATIC INJECTION DEVICE WITH PLUNGER VELOCITY REGULATOR

CROSS-REFERENCE TO RELATED APPLICATIONS

This application represents the U.S. National Stage of International Application No. PCT/GB2016/051471 filed on May 20, 2016, which is incorporated by reference in its entirety, and is based upon, claims priority to, and incorporates herein by reference in its entirety, United Kingdom Patent Application Serial No. GB 1508862.8, filed May 22, 2015.

FIELD OF THE INVENTION

This invention relates to injection devices for delivering a dose of medicament from a syringe. In particular, but not exclusively the invention relates to an autoinjector type device.

BACKGROUND OF THE INVENTION

Injection devices are used for the convenient administration of medicaments. For example, injection devices (which may typically be in the form of a pen injector) may be used for providing a single metered dose of a medicament, for example such as Epinephrine in an emergency or for providing regular metered doses of a medicament, such as Insulin. Such devices may be either single use "disposable" devices in which the device is typically provided with a syringe already installed, and which is not user-replaceable, or "reusable" devices which allow the user to replace the syringe when the medicament has been used.

It may be noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may formed integrally with the (or part of the) injection device.

Injection devices may be provided in the form of an "autoinjector" device, in which, in addition to automating the delivery of the medicament, the device is also arranged to automate the insertion of a needle into the skin prior to the delivery of the medicament.

Injection devices generally comprise a delivery arrangement which is arranged to automatically deliver a dose from the syringe, and optionally (in the case of an autoinjector) to first displace the syringe within the housing to cause needle penetration. The delivery arrangement generally acts via a plunger which includes or engages a piston (also referred to as a "bung") which is slidably provided within the syringe. In the case of an autoinjector the initial stiction between the bung and syringe may resist forward movement of the piston relative to the syringe such that initially the delivery arrangement moves the syringe into the needle insertion position (whereupon further movement of the syringe is blocked and the delivery arrangement will continue to move forward thus moving the bung). A common form of delivery arrangement includes an actuation mechanism which biases the plunger forwardly and a trigger mechanism which holds the plunger (directly or indirectly) against the force of the actuation mechanism until the trigger is released. For example the actuation mechanism may comprise a drive spring (for example a compression spring) which is held in an energised (or primed position) prior to release by the trigger.

It will be appreciated that the force required to be provided by the actuation mechanism may depend upon a number of factors and these must be taken into account when designing the injector device. For example the force may depend upon the volume of medicament to be delivered, the viscosity of the medicament and/or the bore of the delivery needle. Whilst some combinations of medicament and syringe/needle size may require relatively high delivery forces the designer must also provide consideration for the reaction of the forces, particularly through the syringe or cartridge body (which for medicament compatibility reasons may be required to be constructed of glass). For example, embodiments of the invention may be particularly useful for use in devices in which a spring force of 30N or more is utilised. Such problems may be especially relevant to autoinjector type devices where it is necessary to arrest the forward movement of the syringe when the needle reaches the required insertion depth. Thus, the applicants have recognised that in some injection devices there may be a risk that the actuation mechanism is required to impart sufficiently high force to the plunger that there is a risk that the initial impact speed between the plunger and bung or between the syringe and the housing may be unacceptably high (for example resulting in an increases risk of damage to the syringe).

At least some embodiments of the invention seek to provide an improved injection device which may help to address some of these problems.

SUMMARY OF THE INVENTION

Accordingly, the invention provides an injection device for delivering a dose of medicament from a syringe, the injection device comprising:
  a housing;
  a plunger moveably mounted within the housing;
  an actuation mechanism arranged to provide a forward biasing force to urge the plunger forward in use to express a dose of medicament;
  a trigger mechanism arranged to (directly or indirectly) releaseably hold the plunger against the force of the actuation mechanism; wherein the injection device further comprises:
  a plunger velocity regulator comprising:
    a cam surface associated with one of the housing or the plunger, and
    a cam member associated with the other of the plunger or the housing and arranged to engage the cam surface during actuation movement of the plunger such that axial movement of the plunger relative to the housing causes relative rotational movement of the cam member and limits the forward velocity of the plunger movement.

It will be appreciated that the "association" with the housing/plunger may mean that the cam member or cam surfaces is either on, or coupled to, the housing/plunger.

In some embodiments the cam surface is on, or fixed relative to the housing and the cam member is associated with (for example axially fixed with) the plunger.

The cam surface may be a forwardly sloped inclined cam surface. The cam surface may be circumferentially extending, and may be for example substantially helical. The cam surface may be formed as part of groove or slot. For example, the cam surface may deformed by the forward wall of a slot. The velocity regulator may, for example, be limited by up to 75% of the normal velocity at which the plunger would be displaced in a corresponding device without the inclusion of the regulator.

The velocity regulator may be configured such that the cam member engages the cam surface during only a portion of the movement of the plunger. For example, the cam surface may only extend over a limited axial portion. The engagement may generally correspond to an initial portion of the movement of the plunger. However, it will be appreciated that there may be a degree of free movement of the plunger before the cam surfaces of the velocity regulator are brought into engagement (for example to allow for manufacturing tolerances within the device and/or to avoid any interference with the initial triggering of the actuation mechanism).

For example, the velocity regulator may limit the speed of the plunger for the first 15% to 20% of the total movement of the plunger required to deliver a complete dose.

The limited axial extent of the cam surface may correspond to the axial position of the cam member during an initial movement of the plunger. In other words, the plunger velocity regulator may only be active during an initial movement of the plunger (for example a rearward portion of the plunger stroke). Such an arrangement may, for example, be provided such that the velocity regulator only limits the speed of the plunger movement during an initial movement of the plunger (which may for example be until the plunger has engaged the bung or until the syringe has reached the required insertion depth). After this period the plunger may be free to accelerate under the force of the actuation mechanism.

The injection device may be an autoinjector. Actuation mechanism may be configured to initially urge the plunger forwardly in use displace the syringe within the housing to cause needle penetration. Subsequent continued movement of the actuation mechanism may urge the plunger forward relative to the syringe express a dose of medicament therefrom. The velocity regulator may be configured to limit the speed of the plunger during the needle penetration stage. The full force of the spring may be exerted on the plunger during at least a portion (for example substantially the fill movement) of the plunger relative to the syringe. Thus, the cam arrangement may only be engaged for an axial extent of the plunger movement which generally corresponds to the needle insertion action in use.

The velocity regulator may disengage after an initial movement of the plunger. For example, the plunger may continue to move forward under the drive of the actuation mechanism after the disengagement of the velocity regulator.

The disengagement of the velocity regulator may be triggered as a result of the relative rotation of the cam member. For example, the rotation of the cam member due to engagement of the cam surface may, after the initial movement, cause the cam member to move free of engagement with the cam surface (for example upon reaching the forwardmost end of the cam surface). In the pre-fired condition, in which the trigger mechanism holds the plunger, the cam member may be in engagement with a rearward portion of the cam surface.

The disengagement of the velocity regulator may be achieved by the cam member disengaging from the plunger. Thus, after disengagement the motion of the plunger may no longer be linked to the movement of the velocity regulator. Alternatively or additionally, the cam member may be arranged to disengage from the cam surface as part of the disengagement of the velocity regulator. For example, the cam member may disengage from the cam surface and continue to travel forwardly beyond the cam surface within the injection device.

The velocity regulator may further comprise a collar including the cam member. The collar may be axially coupled to the plunger. The collar may be configured to rotate relative to the plunger during actuation movement of the plunger. For example, during initial movement of the plunger the cam member may travel along the forwardly sloped circumferentially extending cam surface resulting in rotation of the collar. As the collar and plunger are axially coupled the movement of the cam members of the collar along the cam surface may limit the forward velocity of the plunger.

The rotation of the collar relative to the plunger may decouple the plunger from the collar. For example, once the collar has rotated by a predetermined angular degree relative to the plunger it may axially decouple from the collar such that the plunger may move forward freely of the collar. For example, one of the collar or plunger may be provided with a keyway and the other of the plunger or collar may be provided with a correspondingly profiled portion which may rotationally disengage from the keyway. For example the collar and plunger may be provided with a bayonet type interconnection arranging. The collar may comprise a keyway and the plunger may comprise a correspondingly profiled portion for engaging the keyway. The keyway may, for example, be formed in a radial flange of the collar.

The corresponding profiled portion of the plunger may include at least one radial projection. The radial projection may be aligned with the keyway by relative rotation of the collar and plunger to allow the plunger to decouple from the collar (and the profiled portion of the plunger to pass through the keyway). The profiled portion of the plunger may, for example, include a pair of opposed radial projections which extend outwardly from the shaft of the plunger. The profiled portion of the plunger may, for example, be provided proximal to a rearward end of the plunger. The rearwardmost end of the plunger may include a profiled head for engagement by the trigger mechanism and the profiled portion of the portion of the plunger may be provided forwardly of the profiled head.

Embodiments of the invention may be particularly suitable for use in an injection arrangement in which the actuation mechanism includes a pair of parallel acting drive springs. Thus, the collar may be further configured to provide an intermediate drive member of the actuation mechanism. The actuation mechanism may comprise a first compression drive spring disposed between the collar and the housing, or a feature fixed relative to the housing, to urge said collar forward during actuation movement and a second compression spring disposed between the collar and the plunger to urge the plunger forward during actuation movement. The first and second compression springs may be coaxial.

The first compression spring may be released immediately upon release of the plunger by the trigger mechanism. Thus, the first compression spring may cause the initial movement the plunger and velocity regulator. The second compression spring may be released upon decoupling of the collar and plunger. For example, prior to the decoupling of the collar and plunger the second compression spring may be held in an energised position between the collar and plunger.

The trigger mechanism may engage the plunger during activation and be configured to prevent rotation of the plunger. For example, the trigger mechanism and plunger may be provided with a splined engagement. The trigger mechanism may also be non-rotationally engaged with the housing of the injection device. The trigger mechanism may, for example, comprise an axially moveable trigger button provided at the rearward end of the injection device. Forward movement of the trigger button may bring an activation feature into splined engagement with the rearward head of the plunger. Thus, the boss may for example cause the plunger to be released from a latch mechanism in the forward direction whilst also preventing rotation of the plunger. The prevention of rotation of the plunger may, for example, ensure that the collar rotates relative to the plunger as a result of the cam member engaging with the cam surface and avoid any rotation of the plunger with the collar due to stiction between the components (since rotation of the plunger may otherwise effect the sequencing of the release of the velocity regulator).

The cam surface may comprise a helical surface. The cam surface may be an internal groove or stepped face in the interior of the housing of the injection device. The cam surface may, for example, be provided on a cam body which is fixed relative to the housing. For example, the cam body may be resiliently engaged with an end surface of the housing (for example, in a snap fit type arrangement). The provision of a separate cam body may provide a convenient means of assembly of the device since the cam members can be positioned rearwardly of the cam surface prior to the cam body being fixed relative to the housing. However, it will also be appreciated that in some embodiments reduction of the number of components may be desirable and, accordingly, the cam surface may be integrally formed, for example on an interior surface associated with the housing. For example a helical thread may be formed on an internal surface of the housing (or a component fixed relative to the housing such as a latch member) which substantially surrounds the plunger.

The cam member may comprise at least one radially outwardly extending lug. For example, the cam member may comprise an opposed pair of outwardly radially extending lugs. The, or each, lug may include a forward facing surface which engages a corresponding rearwardly facing surface of the cam surface. The cam surface may comprise a corresponding plurality of cam surfaces, for example, a pair of opposed cam surfaces. The cam surfaces may, for example, define parallel cam paths. For example, the cam paths may be formed in the manner of an internal screw thread relative to the housing of the injection device.

Whilst the invention has been described above, it extends to any inventive combination of the features set out above or in the following description or drawings.

DESCRIPTION OF AN EMBODIMENT

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use.

Axial, radial and circumferential are used herein to conveniently refer to the general directions relative to the longitudinal direction of the injection device (or components thereof). The skilled person will, however, appreciated that these terms are not intended to be narrowly interpreted (and for example, the injection device may have a non-circular and/or irregular form). Typically, regardless of the chosen injection device external profile the syringe or cartridge will have a conventional, generally cylindrical, elongate form and will include or be associated with a needle extending longitudinally from a forward end thereof. Thus, the longitudinal axis of the injection device will typically substantially coincide with (or be parallel to) the axial direction of the syringe or cartridge.

Figure 1:
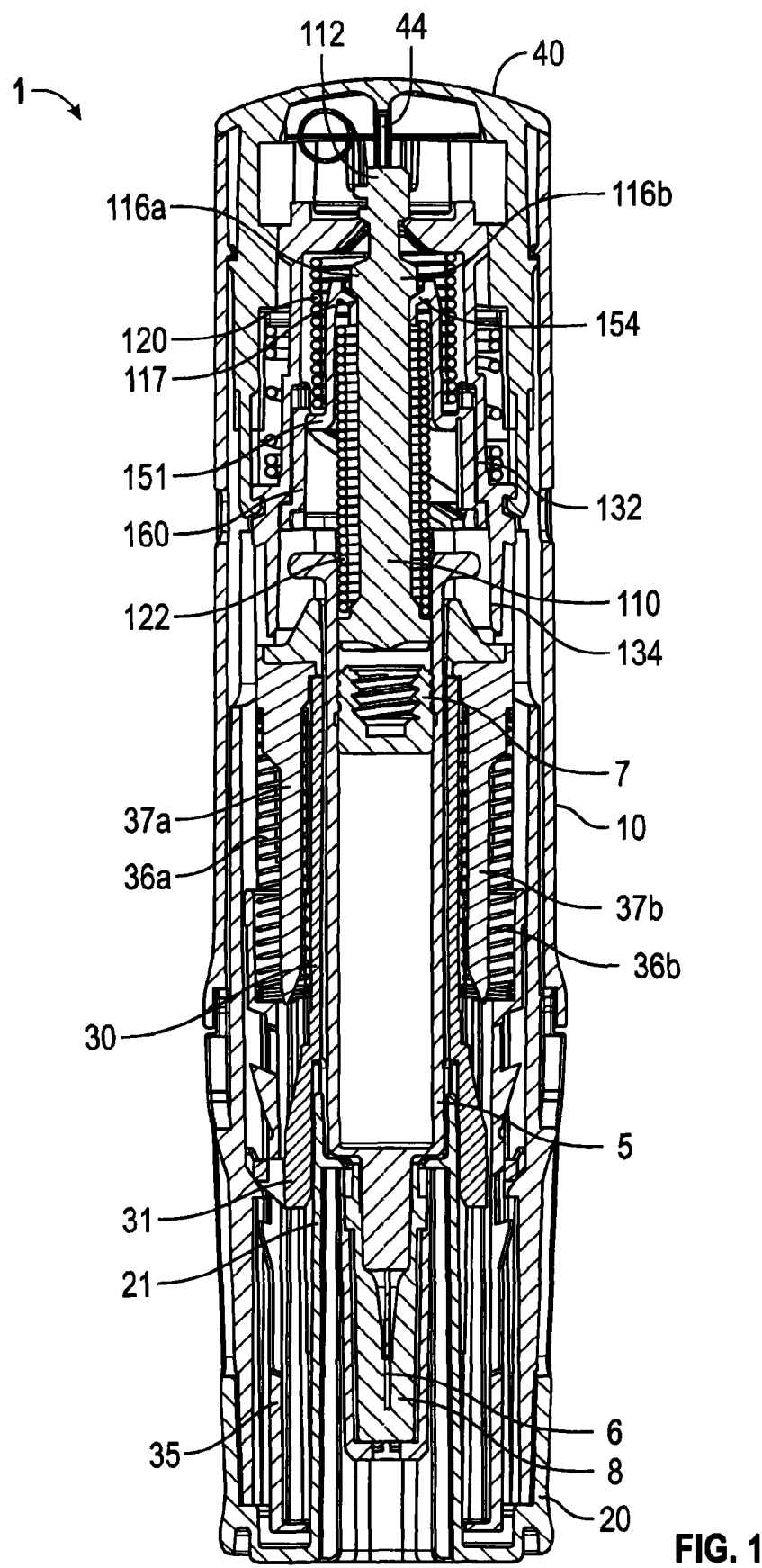
FIG. 1 shows a cross-sectional view of an autoinjection device in accordance with an embodiment of the invention.

FIG. 1 shows a cross sectional view of an autoinjector 1 in accordance with an embodiment of the invention. The autoinjector comprises a housing 10 within which is provided a syringe 5 of medicament. The housing 10 has a generally elongate tubular shape with a generally oval cross-sectional profile (and has a longitudinal axis running through the centre of the syringe).

The syringe 5 is a conventional syringe having a bung 7 within its body and a needle 6 at its forward end which may initially be protected (so as to remain sterile) by a removable needle shield 8. The illustrated autoinjector 1 is generally intended to be a single use device (although the skilled person will appreciate that the invention is not limited to such devices) and, therefore, the view of FIG. 1 may typically represent a fully assembled, ready to use device as provided to an end user would typically be provided (with the autoinjector 1 preassembled around the syringe 5). A cap 20 is provided which closes the forward end of the autoinjector 1 prior to use. The cap 20 may include an internal formation, comprising rearwardly extending members 21, arranged to engage the removable needle shield 8 of the syringe 5 such that removal of the cap 20 from the housing 10 during use also removes the removable needle shield 8 from the syringe 5.

The autoinjector 1 may conveniently be considered to comprise a forward subassembly in a forward portion of the housing 10 and a rearward assembly in a rearward portion of the housing 10. The two housing portions may be snap fit together during assembly. The forward subassembly may comprise the components which surround and/or are initially forward of the syringe 5. The rearward subassembly may comprise those components which are initially rearward of the syringe 5. The present invention is associated with the actuation mechanism 30 which is in the rearward subassembly and as such the forward components may be of any convenient known arrangement. As such the forward components will be only briefly described herein.

A forward portion of the housing 10 may contain a syringe carrier 30 for movably mounting the syringe within the housing 10 to enable automatic needle penetration. It may be noted that prior to the removal of the cap 20, the rearwardly extending members 21 of the cap 20 underlie spring fingers 31 of the syringe carrier 30. This arrangement, thus prevents inward movement of the spring fingers 31 prior to removal of the cap 20 and, therefore, blocks unlatching of the syringe carrier 30 and prevents movement relative to the housing 20.

A needle shroud 35 is also provided and arranged to shroud the needle after use (when the syringe 5 and syringe carrier 30 are in a forward position) to prevent needle stick injuries. The shroud 35 is activated by a pair of side-by-side shroud springs 36a, 36b carried on respective spring guides 37a, 37b. The present application is not limited to any arrangement of the syringe carrier 30 and/or needle shroud 35 (and some embodiments may even omit one or both of the features). As such the operation of the shroud 30 and carrier 35 is not described herein. However, it may be noted that the arrangement substantially corresponds to the arrangement of the Applicants' earlier International Patent Application PCT/GB2011/052557.

A rearward portion of the housing 10 includes a trigger button 40 which is inserted into the rearward portion of the housing 10 from the rearward end so as to substantially close the rearward end of the housing 10. The trigger button 40 has a cup-like profile with side walls which are arranged to fit within (and be substantially concentric with) the rearward housing 30 and an end wall which closes the rear end of the housing. The trigger button 40 includes a pair of forwardly extending resilient arms 41a and 41b which are arranged to provide an engagement between the trigger button 40 and the injector 1.

The rearward portion of the housing 10 also includes the drive mechanism 100. The drive mechanism 100 includes a plunger 110 which is arranged to engage the bung 7 of the syringe 5 in use. The plunger 110 is driven forwards in use by a pair of concentric drive springs 120 and 122 (although it will be appreciated that in other embodiments a single spring may be used). An intermediate drive member in the form of a collar 150 (which also functions as part of the velocity regulator as described below) is provided between the first 120 and second 122 drive springs. A pair of thrust washers 121, 123 are provided respectively between the first 120 and second 122 springs and the drive member/collar 150. A latch 130 is arranged concentrically around the drive springs 120, 122, intermediate member/collar 150 and plunger 110. The latch 130 is arranged to hold the plunger 110 against the bias of the springs 120, 122 until the latch is released via the trigger button 40. The latch 130 comprises a rear body portion 132 having a split cylinder profile and defining a latch aperture at its rear end and a forward connecting body portion 134. The basic functional operation of the drive mechanism 100 is substantially as described, for example, in the applicants' earlier International Patent Applications PCT/GB2011/051950 and PCT/GB2014/052276.

Figure 2:
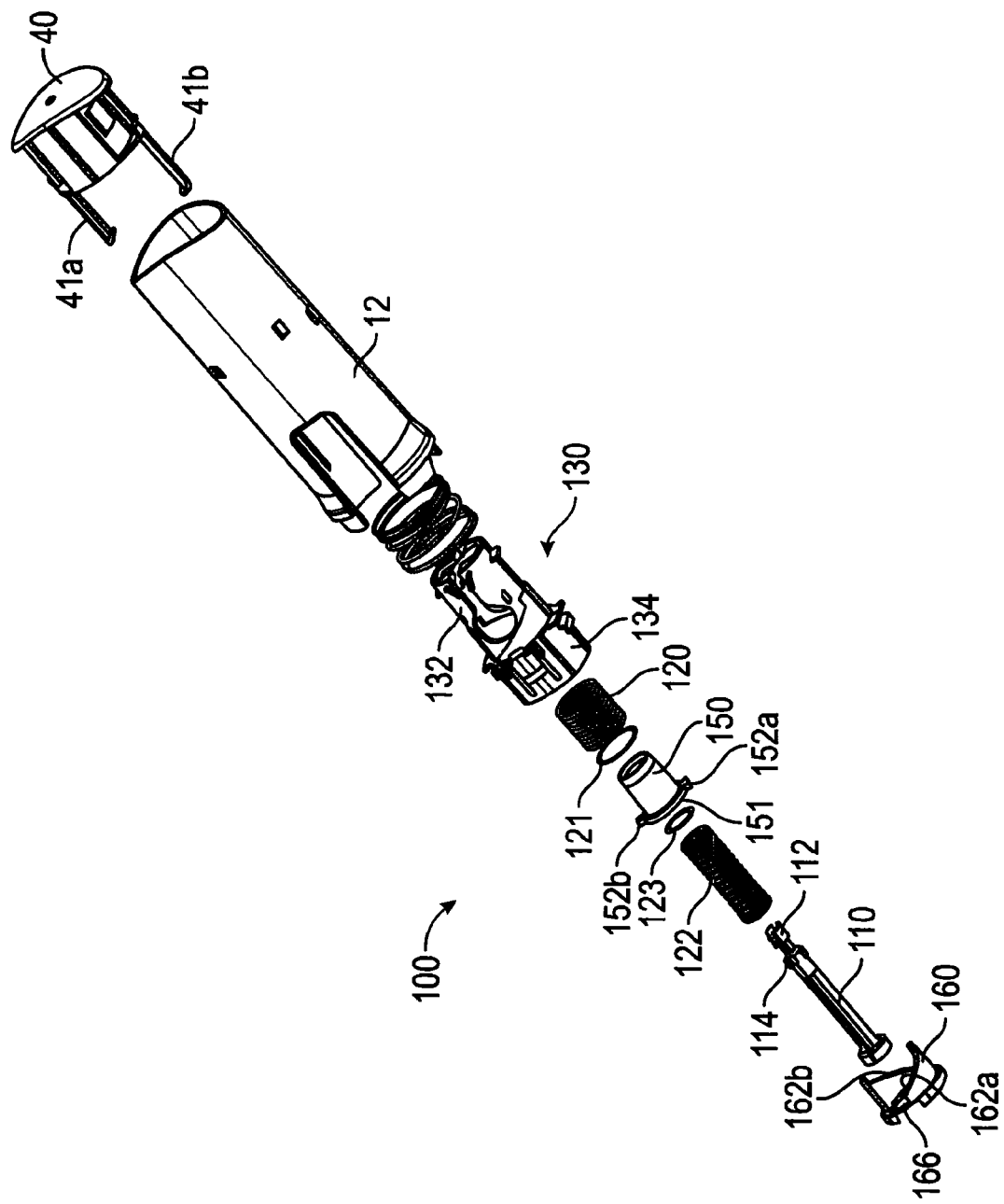
FIG. 2 shows an exploded three-dimensional view of a rearward sub-assembly of the device of FIG. 1.
Figure 3:
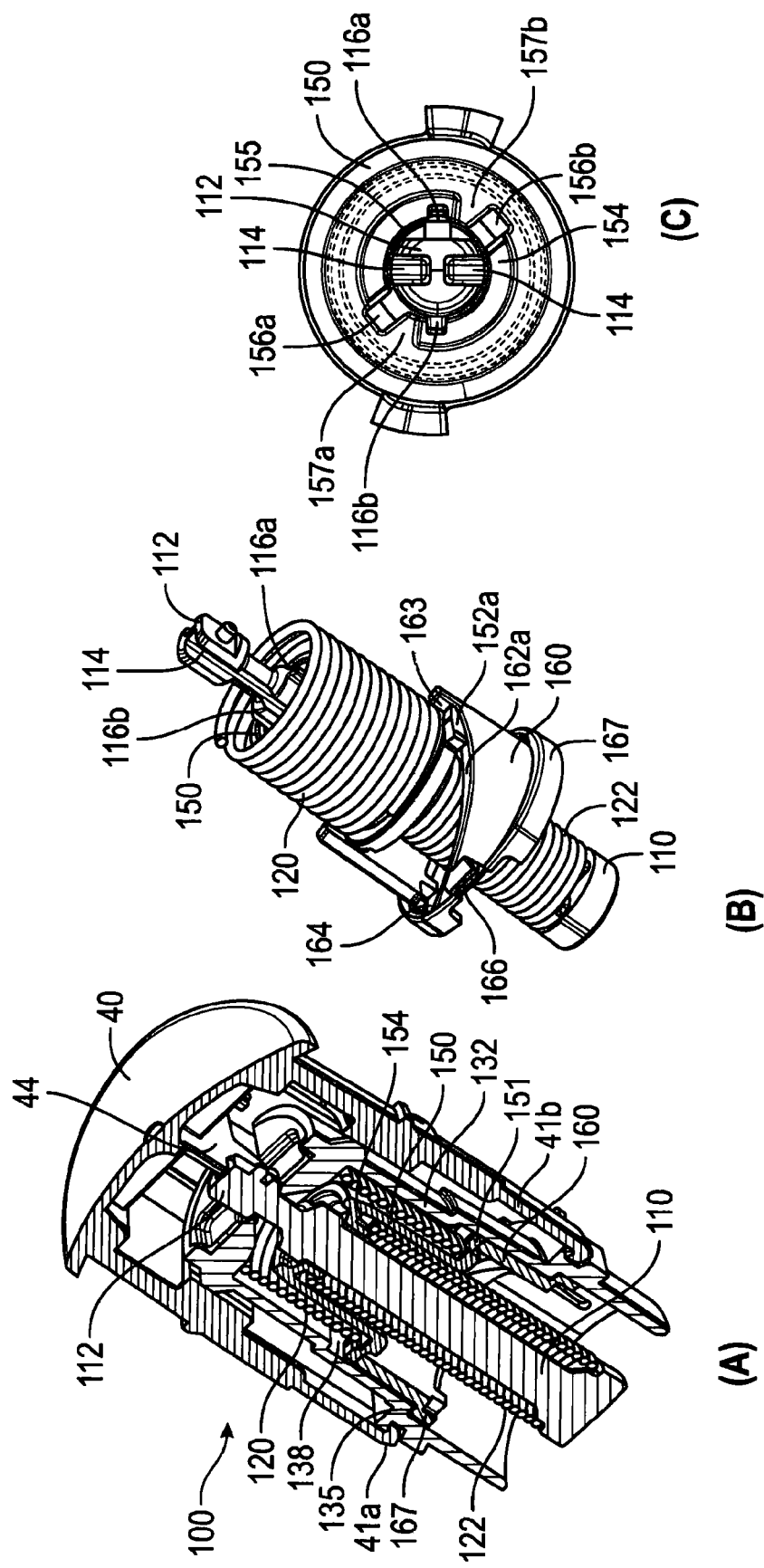
FIG. 3 shows a cross-section, partial three-dimensional view and partial end view of an actuation mechanism including a velocity regulator in accordance with an embodiment of the invention in a pre-fired state.
Figure 4:
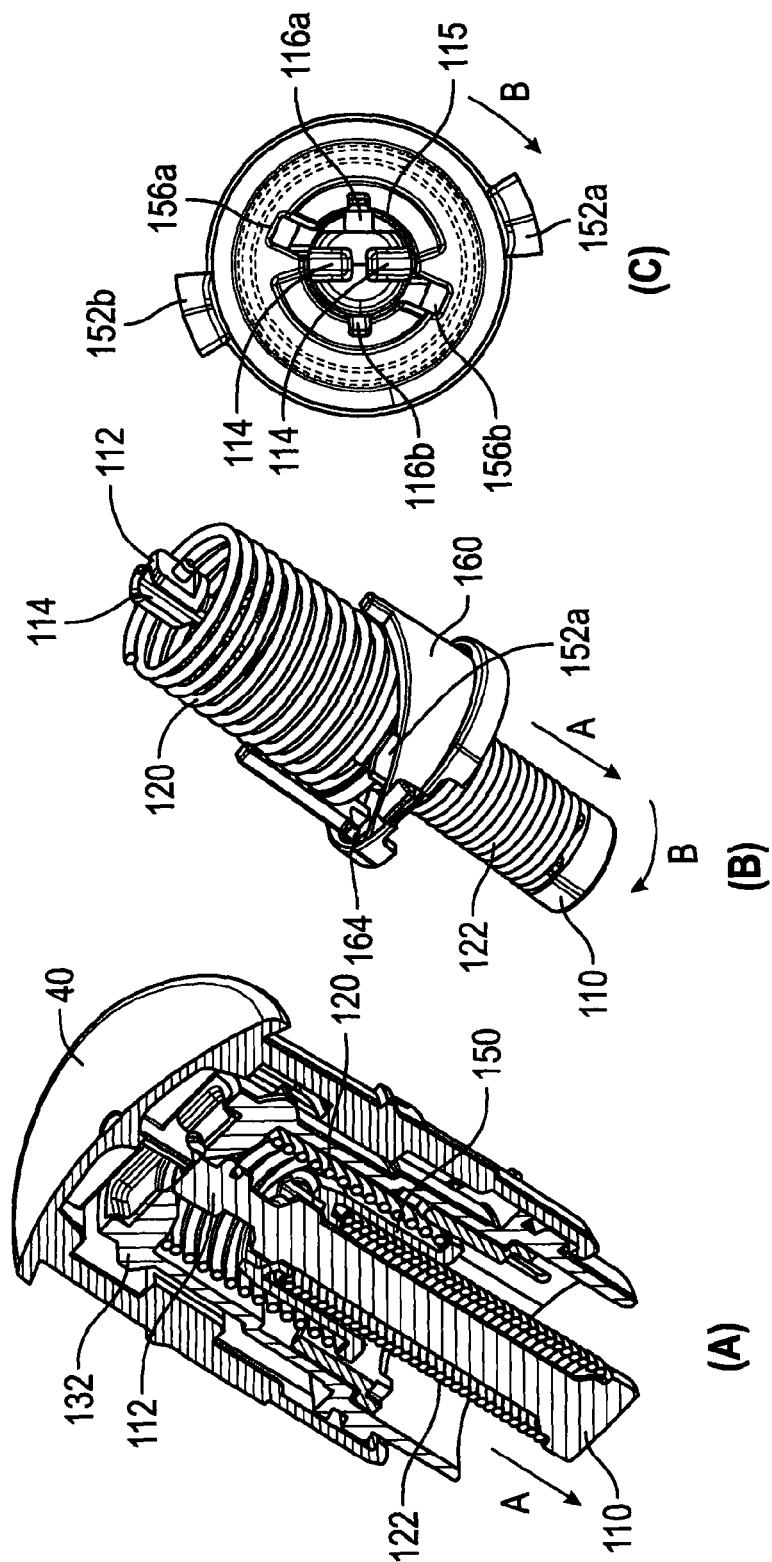
FIGS. 4 to 6 show sequential views corresponding to FIG. 3 during the activation of the autoinjection device.

The actuation mechanism will now be described in further detail with particular reference to FIGS. 2 and 3. FIG. 2 shows an exploded view of a rearward sub-assembly of the autoinjector device 1 (in which it may be noted that the housing 10 includes a discreet rearward housing component 12). In FIG. 3a the housing is omitted for clarity and in FIGS. 3b and 3c only the components directly associated with the velocity regulator are shown for further clarity. As noted above, the actuation mechanism includes a latch member 130 which is removably fixed into the housing 10 (by a snap fit arrangement) and initially retains the plunger 110 against the forward biasing force of the actuation springs 120 and 122 (which act via the intermediate member 150). At the rear of the injection device 1 is provided a trigger button 40 which may initially be retained in position by the pair of arms 41a, 41b. In a central portion of the inner surface of the rearward face of the button 40 a forwardly extending boss 44 is provided which may act to urge the plunger 110 out of engagement with the latch member 130 during activation (in a manner such as that described in the applicants earlier patent applications referred to above). In embodiments of the present invention it will be noted that the boss 44 comprises an arrangement which is in splined engagement with the rearward head 112 of the plunger 110. In the illustrated embodiment, it will be seen that the rearward end of the plunger 110 is provided with a pair of axially extending radial slots which extend forwardly from the head 112 and the boss 44 comprising a corresponding pair of projections. As will be explained in further detail below, this arrangement ensures that the plunger 110 is rotationally fixed relative to the trigger button 40. In turn the trigger button 40 is non-rotationally engaged with the housing 10 (for example, due to the non-circular shape of the housing 10 and trigger button 40 and/or the engagement between the legs 41a, 41b of the trigger button 40 and the latch 130).

The actuation mechanism 100 of the autoinjector device 1 also includes a velocity regulator arranged to control or limit the initial velocity of the plunger 110 upon release of the actuation mechanism. The velocity regulator utilises cam members 152 which travel along a cam surface 162 which provides an inclined plane along which the cam member 152 will travel during actuation.

The cam surface 162 is conveniently provided on a cam body 160 which is engaged with the forward portion 134 of the latch 130 by a snap-fit arrangement including, for example, at least one latch member 166. To ensure proper alignment between the cam body 160 and the latch member 130 an alignment flange 167 may also be provided on the cam body 160 to abut a corresponding shoulder 135 in the latch 130. The cam body 160 may comprise a generally annular body with an external profile which matches the required internal profile of the latch 130. A pair of helical cam surfaces 162a, 162b are defined at the rearward end of the cam body and are forwardly sloped to define a pair of parallel cam paths which extend circumferentially around the interior of the injection device 1 whilst also being inclined forwardly in the manner of a partial screw thread. A correspondingly profiled shoulder may be provided rearwardly of the cam surface 162 on the interior surface of the latch 130 such that when the cam body is assembled with the latch 130 a slot or track 138 as defined (and configured to receive the cam members 152). Each cam surface 162 is provided with a stop 163 at its rearward end (which acts to separate the separate cam paths defined by the cam body 160) and ends with a cut-out or aperture 164 at the forwardmost end of the cam surface 162.

The collar 150 acts as an intermediate drive member between the first compression spring 120 and second compression spring 122. Accordingly, the collar 150 includes an external radial flange 151 at its forward end which provides a seat for the first compression spring 120 and an internal radial flange 154 at its rearward end which provides a seat for the second compression spring 122. The thrust washers 121, 123 are disposed on the seats between the radial flanges 151, 154 of the collar and the springs 120, 122. The collar 150 is a generally cylindrical body and is provided with a pair of radially opposed outwardly extending lugs 152a, 152b. The lugs 152a, 152b are provided on a radially outer surface of the outwardly extending flange 151 (such that they do not impede either of the compression springs 120, 122). The internal flange 154 at the rear of the collar 150 includes an aperture 155 through which the head 112 of the plunger extends when the actuation mechanism 100 is in the pre-fired (or primed) condition as shown in FIG. 3.

The aperture 155 is provided with a keyed profile defined by a cylindrical central aperture portion 155a and a pair of opposed radial slots 156. The cylindrical side walls of the collar 150 extend rearwardly slightly beyond the flange 154 so as to define a cylindrical cup which surrounds the flange 154 and the aperture 155. Inwardly radially extending stop members 157a, 157b may be provided adjacent to one side of the radial slots 156a and 156b.

A rearward portion of the plunger 110 which is axially rearward of the aperture 155 in the pre-fired configuration is provided with a profiled cross-section for engagement with the keyway defined by the aperture 155. This profiled portion is immediately forward of the head 112 of the plunger which is configured to be engaged by the latch 130. The profiled portion is defined by a pair of radially outwardly extending projections 116a, 116b which provide a forward facing shoulder 117 which is initially engaged with the rearward face of the flange 154. The radial projections 116a, 116b are configured such that they may pass through the radial slots 156a, 156b when the slots 156 and projections 116 are aligned.

The actuation sequence of the mechanism 100 and velocity regulator will now be described with reference to FIGS. 3 to 6. The pre-firing configuration of the actuation mechanism 100 is shown in FIG. 3. In this configuration the head 112 of the plunger 110 is retained in the aperture of the latch 130. As such both the first compression spring 120 and the second compression spring 122 are in a compressed, energised, state. The trigger button 40 is in splined engagement with the rearward end of the plunger 110 via the boss 44 being positioned within the slots 114 at the rear of the plunger 110. The rearward portion 132 of the latch 130 is unable to expand to release the head 112 of the plunger 110 as part of the trigger button abuts an outer surface of the rearward section of the latch 132.

In this position the radial projection 116 of the plunger 110 are rearwardly positioned relative to the aperture 155 of the collar 150 and the relative rotational position of the plunger 110 and the collar 150 has been set during assembly such that the projections 116 are misaligned with the slots 116 and, in fact, it will be noted that the projections 156 may be abutting against the stops 157 of the collar 150. In this initial position the cam members 152 are positioned at a rearward end of the cam surfaces 162 and essentially abut against the stops 163 at the rearwardmost end of the cam surfaces 162.

In order to activate the device the user urges the trigger button 40 forwardly relative to the housing 10 of the autoinjector device 1 (having firstly carried out any required initiation steps such as removal of the cap from the forward end of the autoinjector device 1 and/or releasing any safety mechanisms, such as an interlock). The forward movement of the trigger button 40 moves the blocking arrangement of the cap 40 out of alignment with the rearward section 132 of the trigger 130 and may also directly transmit a forward force onto the rear of the plunger 110 via the engagement of the boss 44 with the head 112 of the plunger 110. As the result of this trigger action, the head 112 of the plunger 110 is released from the trigger 130 freeing the rearward spring 120 to urge the plunger forwardly, in the direction of arrow A, via the outer flange 151 or the collar 150.

This forward movement causes the cam members 152a, 152b to travel along the inclined path of the cam surface 162a, 162b. As the first spring 120 expands its axial force is transmitted by the collar 150 through the fully compressed second compression spring 122 to the forward end of the plunger 110. However, initially the plunger 110 is unable to travel beyond the collar 150 as the radial projections 116 engage the internal flange 154 at the rear of the collar 150.

Due to the splined engagement between the trigger button 40 and the plunger 110 the collar 150 must rotate relative to the plunger 110, in the direction of the arrow B, as the cam members 152a, 152b travel along the cam surfaces 162a, 162b. The thrust washers 121, 122 prevent or reduce any frictional resistance to the rotation of the collar 150 by the springs 121, 122. As best seen in the end view of FIG. 4c the resulting relative rotation of the collar 150 causes the aperture 155 to rotate relative to the radial projections 116a, 116b moving the projections off the stop surface 157 and towards the radial slots 156a, 156b.

Figure 5:
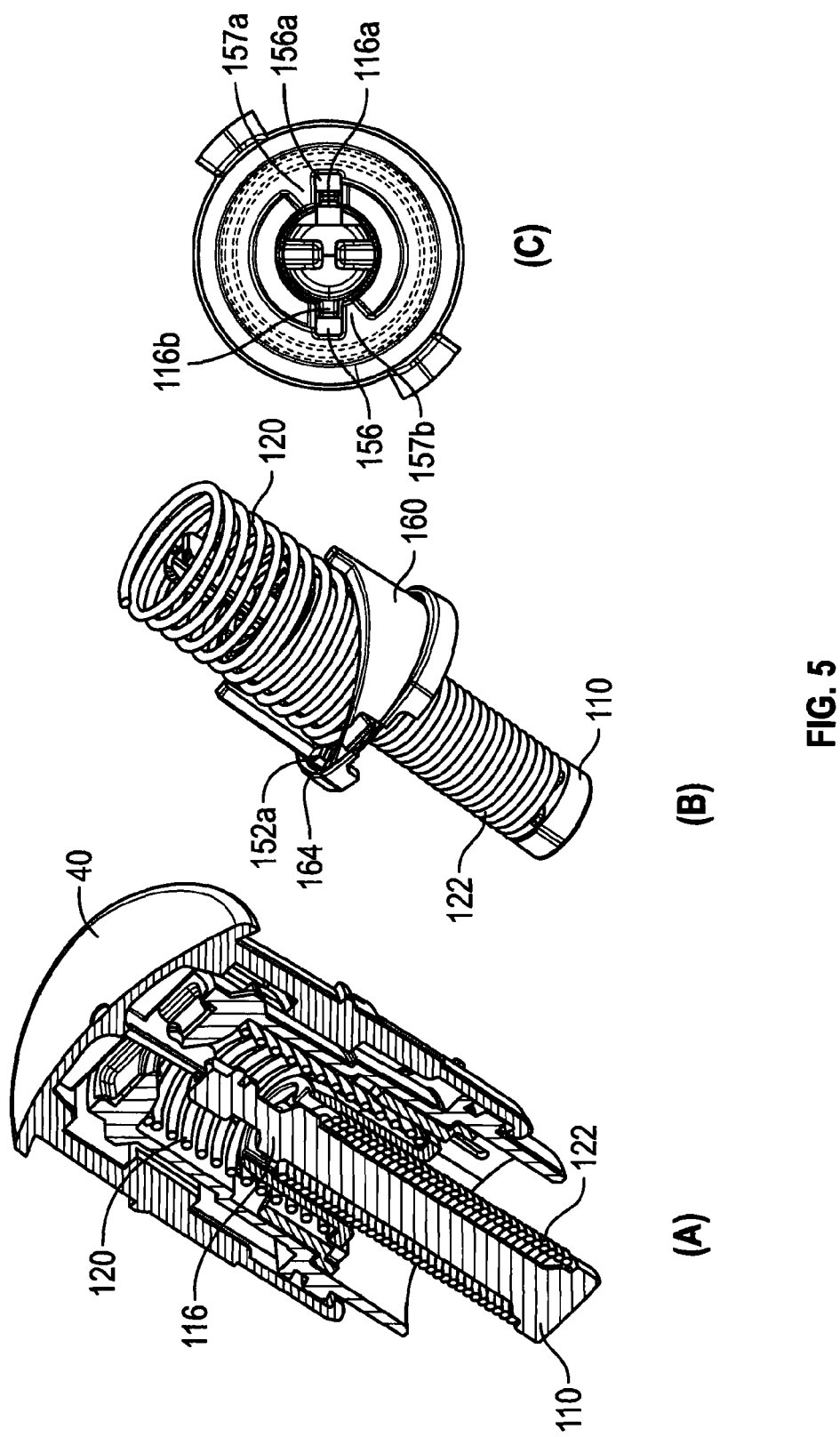

As the plunger 110 and collar 150 continue to move forwardly the collar 150 reaches its fully rotated position as shown in FIG. 5. In the illustrated example the fully rotated position corresponds to approximately one half turn of the collar 150 (although the skilled person will appreciate that the particular configuration may vary depending on the profile of the cam surface and the required sequencing of the actuation mechanism 100). In this position the radial slots 156a, 156b have rotated into alignment with the radial projections 116a, 116b and the cam members 152a, 152b have also reached the end of the cam surface 162a, 162b and have moved into alignment with the cut-out/aperture 164 at the end of the cam path.

Figure 6:
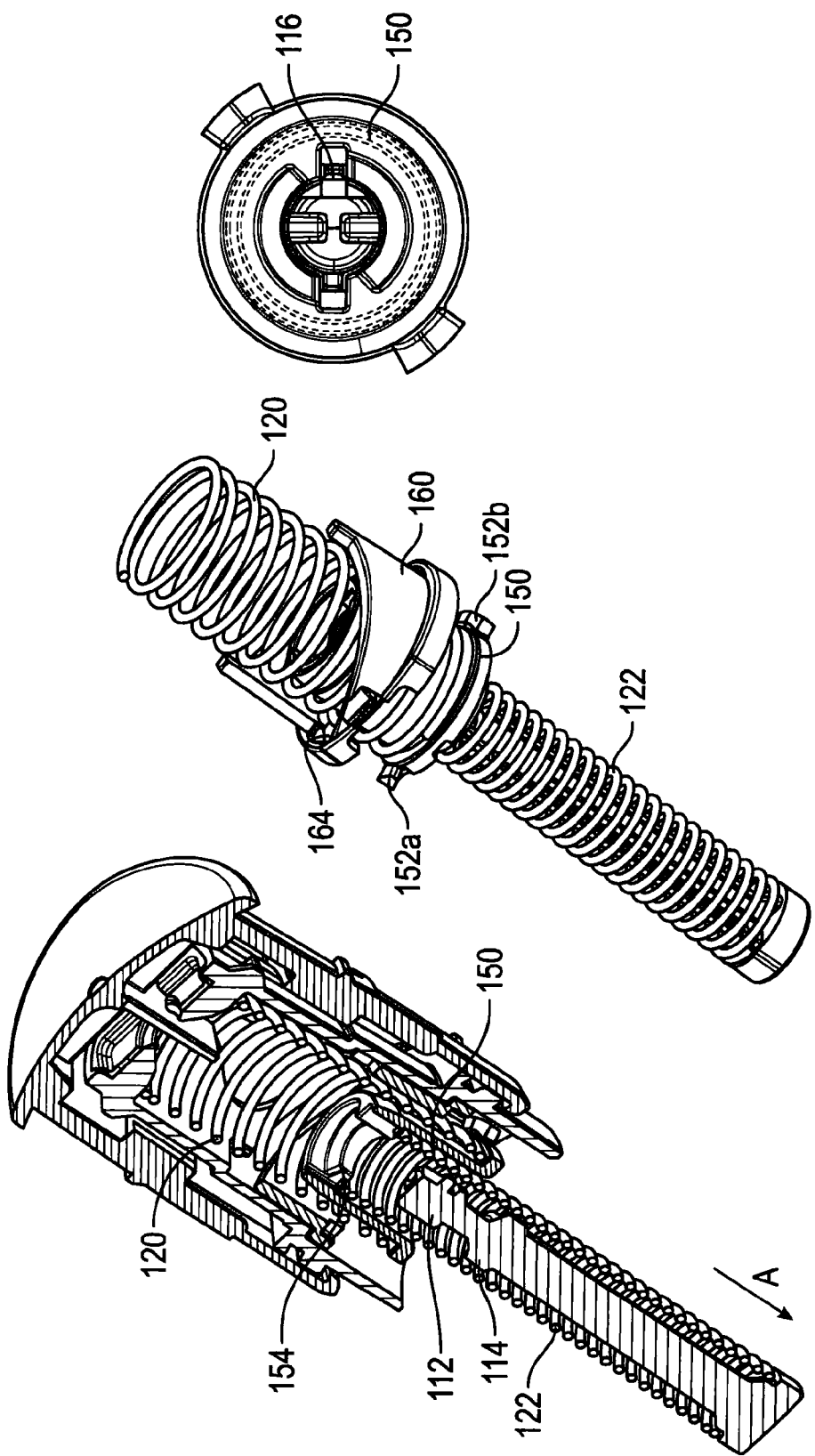

Accordingly, as shown in FIG. 6 the velocity regulator may now disengage so as to allow the plunger to continue freely forward (continuing in the direction of arrow A). In this forward movement the plunger 110 moves forward relative to the collar 150 due to the radial projections 116a, 116b passing through the radial slots 156a, 156b and the collar 150 is also allowed to pass forwardly of the cam body 160 due to the cam members 152a, 152b passing through the cut-outs 164. In other words, both the collar 150 and plunger 110 are disengaged and the collar 150 and cam body 160 are disengaged. In the illustrated embodiments the disengagements both occur substantially simultaneously (although the skilled person will appreciate that this may depend on the particular sequencing required). Once the velocity regulator is disengaged the forward motion of the plunger 110 is no longer regulated (but the skilled person will appreciate that the plunger may now be pressing against the medicament within the syringe 5 such that its motion is naturally damped).

Although the invention has been described above with reference to a preferred embodiment, it will be appreciated that various changes or modifications may be made without departing from the scope of the invention as defined in the appended claims. For example, the skilled person will appreciate that the timing of the disengagement between the components of the velocity regulator may depend on the particular configuration of the device. For example, the velocity regulator may be intended to slow/control the movement of the plunger 110 only during an initial movement in which the plunger 110 is brought into contact with the bung 7 of the syringe 5 (since manufacturing tolerances will usually make it necessary for the forward end of the plunger 110 to be initially spaced from the rearward end of the bung 7) so as to reduce impact thereto. Alternatively, or additionally, the velocity regulator may be configured to control the speed of movement of the actuation mechanism until the needle insertion step of the actuation process has been completed.

Whilst the illustrated example includes two opposing counter-surfaces the skilled person will appreciate that more or less features may be utilised in embodiments of the invention.

In the illustrated embodiment the cam surface defines a substantially constant helical cam path but the skilled person will appreciate that the surface may have other sloped profiles (for example, a variable angle of incline) depending upon the velocity profile required for the forward movement of the plunger 110. Whilst an arrangement having two compression springs is advantageous in providing a compact actuation mechanism the skilled person will appreciate that in some embodiments only a single compression may be utilised. For example, in a single spring arrangement, the cam members could be formed on a portion of the plunger and the plunger may be allowed to rotate relative to the housing.

The invention claimed is:

1. An injection device for delivering a dose of medicament from a syringe, the injection device comprising:
   a housing;
   a plunger moveably mounted within the housing;
   an actuation mechanism configured to provide a forward biasing force to urge the plunger forward in use to express a dose of medicament;
   a trigger mechanism configured to releaseably hold the plunger against the force of the actuation mechanism; and
   a plunger velocity regulator comprising:
      a cam surface associated with one of the housing or the plunger, and
      a cam member associated with the other of the plunger or the housing and configured to engage the cam surface during actuation of the plunger such that an axial movement of the plunger relative to the housing causes a relative rotational movement of the cam member and limits a forward velocity of the plunger;
   wherein the cam member disengages from the plunger to disengage the plunger velocity regulator after a portion of the actuation of the plunger.

2. The injection device of claim 1, wherein the injection device is an autoinjector and the actuation mechanism is configured to initially urge the plunger forwardly to displace the syringe relative to the housing during a needle penetration stage and subsequent continued movement of the actuation mechanism urges the plunger forward relative to the syringe in a medicament expression stage, and wherein the plunger velocity regulator is configured such that the velocity of the plunger is limited during the needle penetration stage and a full force of the actuation mechanism is exerted on the plunger during at least a portion of the medicament expression stage.

3. The injection device of claim 1, wherein the cam surface is on, or fixed relative to the housing, and the cam member is associated with the plunger.

4. The injection device of claim 1, wherein the cam member engages the cam surface only during a portion of the actuation of the plunger.

5. The injection device of claim 1, wherein the relative rotational movement of the cam member disengages the plunger velocity regulator.

6. The injection device of claim 5, wherein the cam member disengages from the cam surface.

7. The injection device of claim 1, wherein the plunger velocity regulator further comprises a collar including the cam member, and wherein the collar is axially coupled to the plunger and rotates relative to the plunger during the actuation of the plunger.

8. The injection device of claim 7, wherein the collar decouples from the plunger by the relative rotation of the collar with respect to the plunger.

9. The injection device of claim 8, wherein the collar comprises a keyway and the plunger comprises a corresponding profiled portion.

10. The injection device of claim 9, wherein the corresponding profiled portion of the plunger includes at least one radial projection, and the at least one radial projection is aligned with the keyway when the collar decouples from the plunger by the relative rotation of the collar with respect to the plunger.

11. An injection device for delivering a dose of medicament from a syringe, the injection device comprising:
   a housing;
   a plunger moveably mounted within the housing;
   an actuation mechanism configured to provide a forward biasing force to urge the plunger forward in use to express a dose of medicament;
   a trigger mechanism configured to releaseably hold the plunger against the force of the actuation mechanism; and
   a plunger velocity regulator comprising:
      a cam surface associated with one of the housing or the plunger;
      a cam member associated with the other of the plunger or the housing and configured to engage the cam surface during actuation of the plunger such that an axial movement of the plunger relative to the housing causes a relative rotational movement of the cam member and limits a forward velocity of the plunger; and
      a collar including the cam member, wherein the collar is axially coupled to the plunger and rotates relative to the plunger during the actuation of the plunger;
   wherein the actuation mechanism further comprises a first compression drive spring disposed between the collar and the housing, or a feature fixed relative to the housing, the first compression drive spring configured to move the collar forward during actuation, and a second compression spring disposed between the collar and the plunger, the second compression drive spring configured to move the plunger forward during actuation.

12. The injection device of claim 11, wherein actuating the trigger mechanism releases the plunger and the first compression spring, and wherein decoupling the collar from the plunger releases the second compression spring.

13. The injection device of claim 1, wherein the trigger mechanism engages the plunger during activation and prevents rotation of the plunger.

14. The injection device of claim 1, wherein the cam surface is provided on a cam body fixed relative to the housing.

15. The injection device of claim 14, wherein the cam surface comprises a helical surface.

16. An injection device for delivering a dose of medicament from a syringe, the injection device comprising:
   a housing;
   a plunger moveably mounted within the housing;
   an actuation mechanism configured to provide a forward biasing force to urge the plunger forward in use to express a dose of medicament;

a trigger mechanism configured to releaseably hold the plunger against the force of the actuation mechanism; and a plunger velocity regulator comprising:
  a cam surface associated with one of the housing or the plunger; and
  a cam member associated with the other of the plunger or the housing and configured to engage the cam surface during actuation of the plunger such that an axial movement of the plunger relative to the housing causes a relative rotational movement of the cam member and limits a forward velocity of the plunger;
wherein the cam member comprises an opposed pair of outwardly radially extending lugs.

17. The injection device of claim 16, wherein the cam surface comprises a pair of opposed cam surfaces defining parallel cam paths.

* * * * *